(12) United States Patent
Mulligan et al.

(10) Patent No.: US 10,150,115 B2
(45) Date of Patent: Dec. 11, 2018

(54) SYSTEM AND METHOD FOR REHYDRATING POWDER AND DELIVERING THE REHYDRATED POWDER TO A REACTOR

(71) Applicant: SpacePharma SA, Delémont (CH)

(72) Inventors: Molly K. Mulligan, Tel Aviv (IL); Alexander Pekin, Ramat Gan (IL); Yair Glick, Petah Tikva (IL); Ira Naot, Zichron Yaacov (IL); Yair Feuchtwanger, Yokneam-Ilit (IL)

(73) Assignee: SpacePharma SA, Delémont (CH)

( * ) Notice: Subject to any disclaimer, the term of this patent is extended or adjusted under 35 U.S.C. 154(b) by 285 days.

(21) Appl. No.: 15/215,642

(22) Filed: Jul. 21, 2016

(65) Prior Publication Data
US 2018/0021772 A1   Jan. 25, 2018

(51) Int. Cl.
| | |
|---|---|
| *G01N 35/10* | (2006.01) |
| *B01L 3/00* | (2006.01) |
| *F16K 15/00* | (2006.01) |
| *F16K 24/04* | (2006.01) |
| *B01J 19/00* | (2006.01) |
| *G01N 35/00* | (2006.01) |

(52) U.S. Cl.
CPC ....... *B01L 3/50273* (2013.01); *B01J 19/0093* (2013.01); *B01L 3/502715* (2013.01); *B01L 3/502723* (2013.01); *B01L 3/502738* (2013.01); *F16K 15/00* (2013.01); *F16K 24/04* (2013.01); *G01N 35/1009* (2013.01); *B01J 2219/0095* (2013.01); *B01J 2219/00891* (2013.01); *B01L 2200/06* (2013.01); *B01L 2300/087* (2013.01); *B01L 2300/0816* (2013.01); *B01L 2400/0478* (2013.01); *B01L 2400/06* (2013.01); *G01N 2035/00237* (2013.01)

(58) Field of Classification Search
CPC ................................ B01L 3/00; G01N 35/10
USPC .......................................... 422/503; 436/179
See application file for complete search history.

(56) References Cited

U.S. PATENT DOCUMENTS

| | | | | |
|---|---|---|---|---|
| 4,783,413 | A | * | 11/1988 | Suter ...................... C12M 41/00 435/286.5 |
| 5,466,220 | A | * | 11/1995 | Brenneman ........... A61J 1/2089 604/411 |

(Continued)

FOREIGN PATENT DOCUMENTS

| | | | |
|---|---|---|---|
| CN | 103695308 | * | 5/2015 |
| JP | 2006-116223 | | 5/2006 |

OTHER PUBLICATIONS

International Search Report for PCT Application No. PCT/IL2017/050804 dated Nov. 21, 2017.

*Primary Examiner* — Arlen Soderquist
(74) *Attorney, Agent, or Firm* — Pearl Cohen Zedek Latzer Baratz LLP

(57) ABSTRACT

A closed system for rehydrating powder and delivering the rehydrated powder to a reactor, may include a liquid reservoir for containing liquid; a syringe configured to contain powder to be rehydrated; a reactor; a controller for controlling operation of the syringe; and a conduit fluidically linking the liquid reservoir to a port of the syringe, fluidically linking the port to the reactor. The controller is configured to operate the syringe so as to draw liquid from the liquid reservoir into the syringe and rehydrate the powder, or to drive the rehydrated powder into the reactor.

16 Claims, 3 Drawing Sheets

(56) References Cited

U.S. PATENT DOCUMENTS

| | | | |
|---|---|---|---|
| 5,766,550 A * | 6/1998 | Kaplan | B01J 4/02 222/325 |
| 6,349,850 B1 | 2/2002 | Cheikh | |
| 6,562,002 B1 * | 5/2003 | Taylor | A61M 5/282 604/82 |
| 6,596,081 B1 * | 7/2003 | Arnowitz | B01D 1/00 117/201 |
| 6,722,054 B2 * | 4/2004 | Yarborough | F26B 5/06 34/284 |
| 7,511,012 B2 * | 3/2009 | Han | C07K 14/00 514/1.1 |
| 8,304,397 B2 * | 11/2012 | Olson | A01K 67/0276 424/93.1 |
| 8,492,140 B2 * | 7/2013 | Smith | C12M 21/08 435/288.2 |
| 8,802,436 B1 * | 8/2014 | Kentner | A61K 35/12 424/551 |
| 2001/0042317 A1 * | 11/2001 | Yarborough | F26B 5/06 34/284 |
| 2003/0207464 A1 | 11/2003 | Lemmo et al. | |
| 2004/0072364 A1 | 4/2004 | Tisone et al. | |
| 2004/0181033 A1 * | 9/2004 | Han | C07K 14/00 530/324 |
| 2006/0141623 A1 * | 6/2006 | Smith | C12M 21/08 435/383 |
| 2009/0180957 A1 * | 7/2009 | Olson | A01K 67/0276 424/9.1 |
| 2010/0047914 A1 * | 2/2010 | Peyman | G01N 33/6863 436/86 |
| 2010/0273680 A1 | 10/2010 | Moore et al. | |
| 2012/0028364 A1 * | 2/2012 | Kraus | G01N 35/1095 436/127 |
| 2012/0330116 A1 * | 12/2012 | Eggers | A61B 5/0275 600/314 |
| 2013/0261046 A1 * | 10/2013 | Chang | A61M 5/31596 514/1.1 |
| 2013/0312868 A1 * | 11/2013 | Ilan | C07K 14/75 141/4 |
| 2015/0024436 A1 * | 1/2015 | Eberhart | C12Q 1/686 435/91.2 |
| 2017/0355584 A1 * | 12/2017 | Naot | B67C 3/28 |

* cited by examiner

SYSTEM AND METHOD FOR REHYDRATING POWDER AND DELIVERING THE REHYDRATED POWDER TO A REACTOR

FIELD OF THE INVENTION

The present invention relates to microgravity systems. More particularly, the present invention relates to a system for rehydrating powder and delivering the rehydrated powder to a reactor.

BACKGROUND OF THE INVENTION

In some cases, effects of gravity may adversely affect an experimental or industrial process. In such cases, it is often desirable to perform the process in a microgravity environment. When a system is in a microgravity environment, all components of the system are subject to identical or indistinguishable gravitational forces. For example, the system may be in free fall or in orbit about a massive body. In such cases, a gravitational contact force between two components of the system, or weight, is absent or practically negligible.

When the process does not require more than a few seconds of microgravity, the process may be performed in a drop tower or similar facility. Slightly longer processes, e.g., that require no more than about half a minute of continuous microgravity, may be performed aboard aircraft that fly in an appropriate pattern (e.g., parabolic arcs). Processes that require longer periods of microgravity (e.g., hours, days, or longer) may be performed aboard unmanned or manned spacecraft. Typically systems that perform processes under microgravity conditions are closed, so as not to allow any materials within the system to escape.

In some cases, a system for performing the process in microgravity may utilize lab-on-a-chip technology or other micro-technology. Use of such technology may enable incorporation of the microgravity system in a platform where available space may be very limited or expensive.

Some such processes require rehydration of powder. Typically such processes are not handled and operated by humans, and therefore require an automated system to perform the process. For example, in U.S. Pat. No. 6,349,850 (Cheikh), there was disclosed a device and method for dehydrating powder that includes a gas-tight syringe to condition under vacuum a dry form of an active principle, a reservoir containing a liquid and a cap forming a connector between the syringe and the liquid reservoir. The injection needle of the syringe is configured to be driven into the septum of the cap. After activation, the extemporaneous preparation is automatic since the device elements move by themselves under the action of the liquid which is drawn by suction into the volume under vacuum containing the solid formulation.

SUMMARY OF THE INVENTION

There is thus provided, in accordance with an embodiment of the present invention, a closed system for rehydrating powder and delivering the rehydrated powder to a reactor. The system may include a liquid reservoir for containing liquid: a syringe configured to contain powder to be rehydrated; a reactor; a controller for controlling operation of the syringe; and a conduit fluidically linking the liquid reservoir to a port of the syringe, fluidically linking the port to the reactor. The controller is configured to operate the syringe so as to draw liquid from the liquid reservoir into the syringe and rehydrate the powder, or to drive the rehydrated powder into the reactor.

In some embodiments, the liquid reservoir, the syringe and the reactor are connected in series by a conduit.

In some embodiments, two one-way valves are provided, one of the one-way valves placed along the conduit in between the liquid reservoir and the syringe, allowing only from the liquid reservoir to the syringe to pass through, and the second of the one-way valves placed along the conduit in between the syringe and the reactor, allowing only from the syringe to the reactor to pass through.

There is also provided a bubble trap positioned along the conduit to trap and vent gas out of the system.

In some embodiments, the system further includes an actuator for actuating a plunger of the syringe.

According to some embodiments, the actuator is selected from the group of actuators consisting of electrical motor, hydraulic motor, and motorized piston.

In some embodiments, the system is provided with powder inside the syringe.

In some embodiments, the syringe includes two pervious membranes inside the syringe defining a space in which the powder is to be placed.

In some embodiments, the reactor is a lab on chip.

There is also provided a method for rehydrating a powder and delivering the rehydrated powder to a reactor in a closed system. The method may include providing a system that includes a liquid reservoir for containing liquid; a syringe configured to contain powder to be rehydrated; a reactor; a controller for controlling operation of the syringe; and a conduit fluidically linking the liquid reservoir to a port of the syringe, fluidically linking the port to the reactor. The method also includes causing the controller to operate the syringe so as to draw liquid from the liquid reservoir into the syringe and rehydrate the powder, or to drive the rehydrated powder into the reactor.

BRIEF DESCRIPTION OF THE DRAWINGS

In order for the present invention to be better understood and for its practical applications to be appreciated, the following Figures are provided and referenced hereafter. It should be noted that the Figures are given as examples only and in no way limit the scope of the invention. Like components are denoted by like reference numerals.

DETAILED DESCRIPTION OF THE INVENTION

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

Some embodiments of the present invention are directed to a closed system operable under microgravity conditions for rehydrating of powder, and for delivering the rehydrated powder to a reactor. By "closed" it is meant that the system does not allow materials to escape the system (other than venting undesired residual gas within the system).

"Powder" in the context of the present invention refers to any substance, such as soluble solid (e.g., powder, granular substance, etc.) or liquid (solution, suspension, etc.) substance, which it to be rehydrated.

Figure 1:
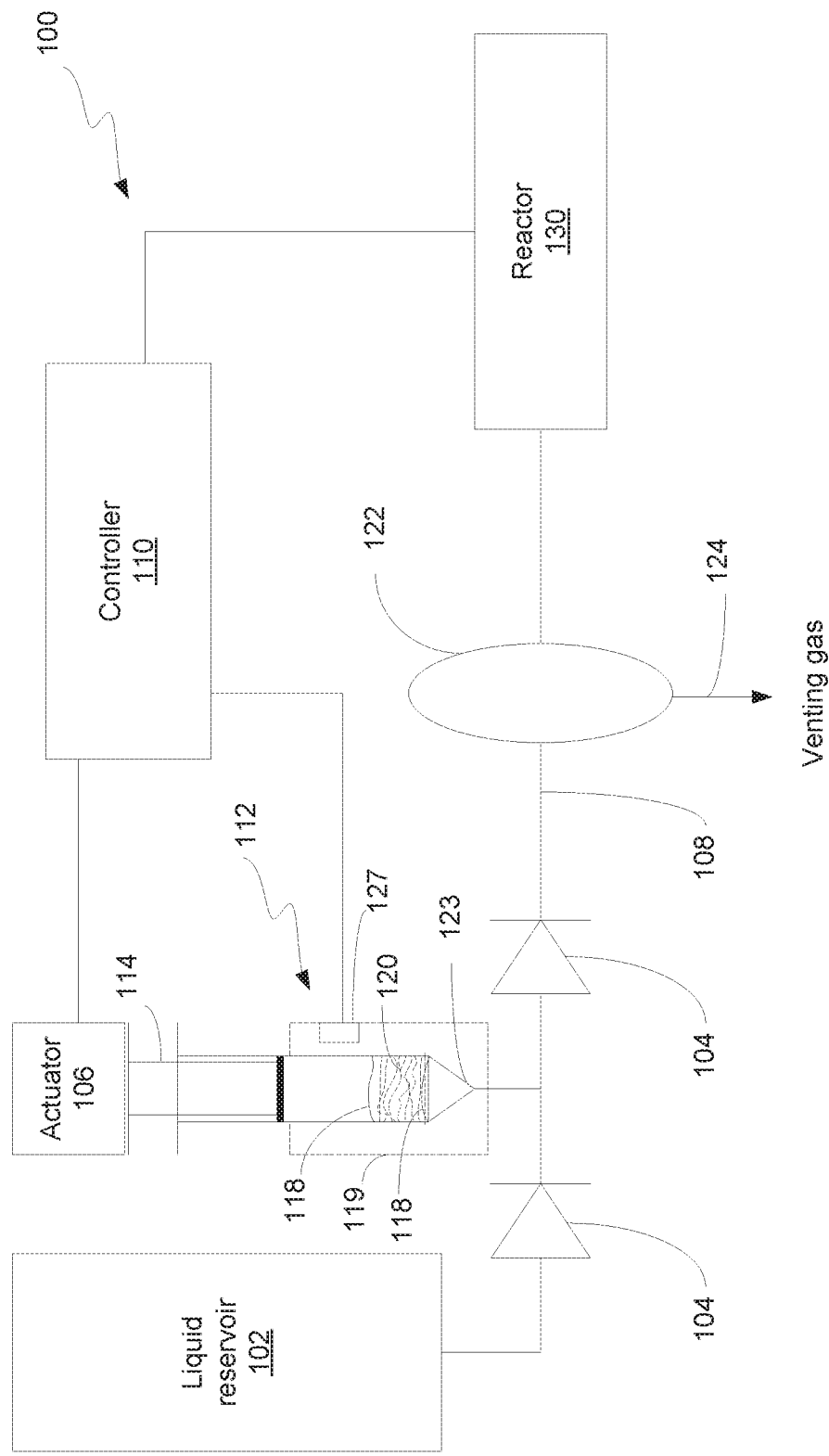
FIG. 1 illustrates a system operable in microgravity conditions for rehydrating powder and delivering the rehydrated powder to a reactor, according to some embodiments of the present invention.

FIG. 1 illustrates a system 100 operable in microgravity conditions for rehydrating powder and delivering the rehydrated powder to a reactor, according to some embodiments of the present invention. System 100 according to some embodiments of the present invention may typically include a reservoir 102 for storing liquid which is to be used in rehydrating the powder. Liquid reservoir 102 is fluidically linked to inlet/outlet port 123 of syringe pump 112 (hereinafter "syringe") via conduit 108, and further to a reactor, in this example, lab on a chip 130, to which at some point it is desired to deliver the rehydrated powder, in the manner described hereinafter.

Two one-way valves 104 are placed along conduit 108, a first one-way valve 104 being positioned between liquid reservoir 102 and port 123 of syringe 112 and the second one-way valve 104 being positioned between port 123 of syringe 112 and bubble trap 122, which is located downstream along conduit 108. Bubble trap 122 is further fluidically linked to reactor 130.

Liquid reservoir 102, syringe 112, bubble trap 122 and reactor 130 are connected in series via conduit 108.

Controller 110 is configured to control actuator 106, which operates plunger 114 of syringe 112, so as to apply suction or force or injection force at port 123 of the syringe 112. The actuator may be, for example, an electric motor with a transmission (e.g., worm gearbox, etc.) designed to move plunger 114 into or out of syringe 112, motorized piston, hydraulic motor, etc. Controller 110 may further be configured to control a process carried out in reactor 130, and may also control ambient temperature of a space 119 within which the syringe 112, or a part of the syringe that contains the powder 120, for example, by operating a temperature controller, such as, for example, electric heater 127.

Two permeable membranes 118 define in between them a space within the containing body of syringe 112 (the powder chamber) which contains the powder 120 separating it from the adjacent portion of the containing body of syringe 112, so as to hold the powder in the vicinity of port 123 of the syringe.

Figure 2A:
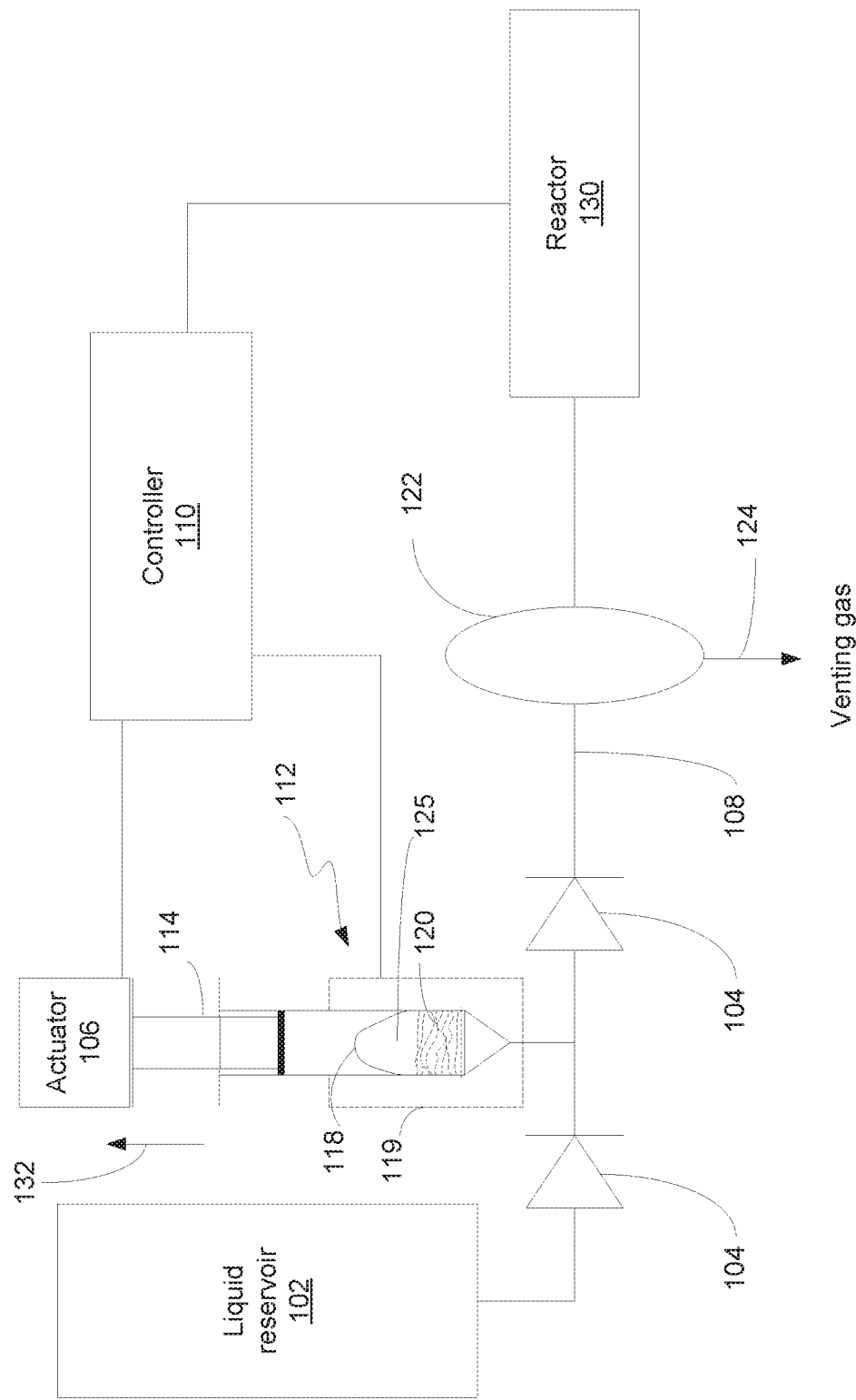
FIG. 2A illustrates a system operable in microgravity conditions for rehydrating powder and delivering the rehydrated powder to a reactor, in a first mixing stage, where liquid is drawn from the liquid reservoir into a remotely operable powder syringe according to some embodiments of the present invention.
Figure 2B:
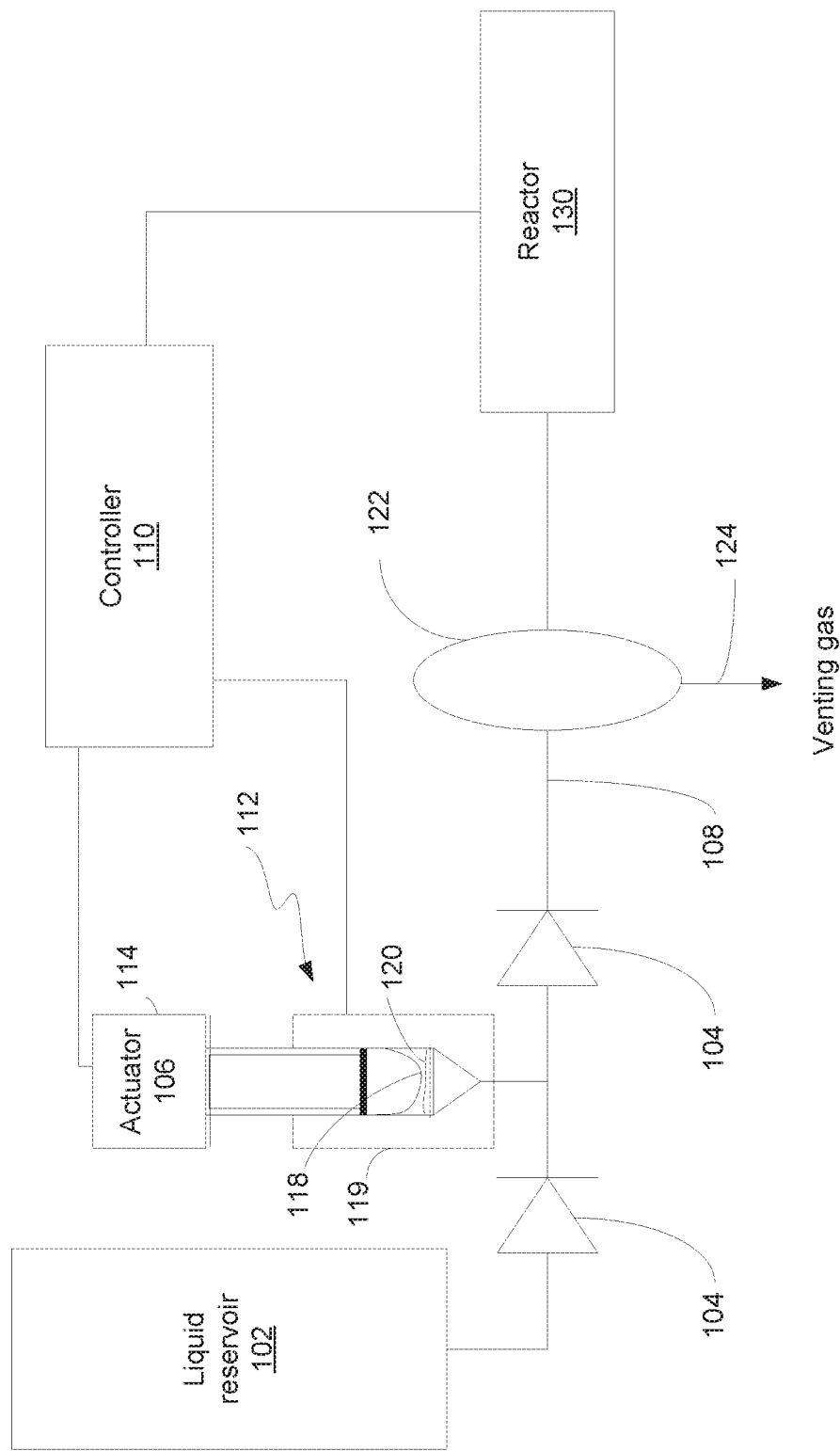
FIG. 2B illustrates a system operable in microgravity conditions for rehydrating powder and delivering the rehydrated powder to a reactor, in a second injecting stage, where the rehydrated powder is injected into the reactor, according to some embodiments of the present invention.

The operation of the system for rehydrating powder and delivering the rehydrated powder is depicted in FIGS. 2A and 2B.

FIG. 2A illustrates a system operable in microgravity conditions for rehydrating powder and delivering the rehydrated powder to a reactor, in a first mixing stage, where liquid is drawn from the liquid reservoir into a remotely operable powder syringe according to some embodiments of the present invention.

A preparatory step is to fill the syringe with the powder, preferably with little to no humidity (e.g., a nitrogen glove box). Then the liquid reservoir is filled with liquid and attached to the circuit as shown in FIG. 2A. These preparatory steps are typically carried out away from the site where the system is to operate. When it is desired to rehydrate the powder, controller 110 activates actuator 106 that draws the plunger 114 out of the containing body of the syringe so to create suction within the syringe, causing liquid to flow from the liquid reservoir via one-way valve 104 into the syringe, rehydrating the powder as it fills the syringe.

FIG. 2B illustrates a system operable in microgravity conditions for rehydrating powder and delivering the rehydrated powder to a reactor, in a second injecting stage, where the rehydrated powder is injected into the reactor, according to some embodiments of the present invention.

Controller 110 activates actuator 106 so as to cause the plunger 114 to move in the opposite direction (into the syringe) thereby applying a force to the dissolved powder within the liquid in order to drive the rehydrated powder mixture to reactor 130, via the second one-way valve 104. A bubble trap 122 in between the second one-way valve 104 and reactor 130 is used to remove gasses from the dissolved powder. The bubble trap is used to vent gasses out 124 of the closed system.

The one way valves 104 are employed to prevent reversing of the flow of liquid into the wrong parts of the system during rehydration and injection of the dissolved powder into the reactor. The one way valves also prevent back diffusion of liquids. The bubble trap allows only liquid to pass into the system and no gas bubbles to pass, ensuring that gas bubbles do not block the system when in use in microgravity. Also, the lack of gas bubbles allows for a more accurate flow, so as to ensure high performance of the system. The thermal control system 127 is used to prevent temperature sensitive powders from being thermally cycled and to ensure the powder remains at the correct storage temperature, if there is a long time period in between filling of powder and liquid into the system, and the actual use of the system to deliver the rehydrated powder into the reactor.

The controller may be mechanical, or electronical controller (e.g., microprocessor), that executes an algorithm that sets the order of operations in line with the required process steps.

Some embodiments of the present invention may be embodied in the form of a system, a method or a computer program product. Similarly, some embodiments may be embodied as hardware, software or a combination of both. Some embodiments may be embodied as a computer program product saved on one or more non-transitory computer readable medium (or media) in the form of computer readable program code embodied thereon. Such non-transitory computer readable medium may include instructions that, when executed, cause a processor to execute method steps in accordance with examples. In some examples, the instructions stores on the computer readable medium may be in the form of an installed application and in the form of an installation package.

Such instructions may be, for example, loaded by one or more processors and get executed.

For example, the computer readable medium may be a non-transitory computer readable storage medium. A non-transitory computer readable storage medium may be, for example, an electronic, optical, magnetic, electromagnetic, infrared, or semiconductor system, apparatus, or device, or any combination thereof.

Computer program code may be written in any suitable programming language. The program code may execute on a single computer system, or on a plurality of computer systems.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A closed system for rehydrating powder and delivering the rehydrated powder to a reactor, the system comprising:
   a liquid reservoir for containing liquid;
   a syringe configured to contain powder to be rehydrated;
   a reactor;
   a controller for controlling operation of the syringe; and
   a conduit fludically linking the liquid reservoir to a port of the syringe, fluidically linking the port to the reactor;
   wherein the controller is configured to operate the syringe so as to draw liquid from the liquid reservoir into the syringe and rehydrate the powder, or to drive the rehydrated powder into the reactor.

2. The system of claim 1, wherein the liquid reservoir, the syringe and the reactor are connected in series by a conduit.

3. The system of claim 1, wherein two one-way valves are provided, one of the one-way valves being placed along the conduit in between the liquid reservoir and the syringe, allowing only from the liquid reservoir to the syringe to pass through, and the second of the one-way valves being placed along the conduit in between the syringe and the reactor, allowing only from the syringe to the reactor to pass through.

4. The system of claim 1, further comprising a bubble trap positioned along the conduit to trap and vent gas out of the system.

5. The system of claim 1, further comprising an actuator for actuating a plunger of the syringe.

6. The system of claim 5, wherein the actuator is selected from the group of actuators consisting of electrical motor, hydraulic motor, and motorized piston.

7. The system of claim 1, provided with powder inside the syringe.

8. The system of claim 1, wherein the syringe comprises two pervious membranes inside the syringe defining a space in which the powder is to be placed.

9. The system of claim 1, wherein the reactor is a lab on chip.

10. A method for rehydrating a powder and delivering the rehydrated powder to a reactor in a closed system, the method comprising:
    providing a system comprising:
      a liquid reservoir for containing liquid;
      a syringe configured to contain powder to be rehydrated;
      a reactor;
      a controller for controlling operation of the syringe; and
      a conduit fludically linking the liquid reservoir to a port of the syringe, fluidically linking the port to the reactor; and
    causing the controller to operate the syringe so as to draw liquid from the liquid reservoir into the syringe and rehydrate the powder, or to drive the rehydrated powder into the reactor.

11. The method of claim 10, further comprising connecting the liquid reservoir, the syringe and the reactor in series by a conduit.

12. The method of claim 10, further comprising providing two one-way valves, placing one of the one-way valves along the conduit in between the liquid reservoir and the syringe, allowing only from the liquid reservoir to the syringe to pass through, and placing the second of the one-way valves along the conduit in between the syringe and the reactor, allowing only from the syringe to the reactor to pass through.

13. The method of claim 10, further comprising using a bubble trap positioned along the conduit to trap and to vent gas out of the system.

14. The method of claim 10, further comprising using an actuator for actuating a plunger of the syringe.

15. The method of claim 10, further comprising filling powder into the syringe.

16. The method of claim 10 performed under microgravity conditions.

* * * * *